United States Patent [19]

Blurton et al.

[11] 4,001,103

[45] Jan. 4, 1977

[54] DEVICE FOR THE DETECTION AND MEASUREMENT OF NO AND $NO_2$ GASES

[75] Inventors: Keith F. Blurton, Yorktown, N.Y.; John M. Sedlak, Norwalk, Conn.

[73] Assignee: Energetics Science, Inc., Elmsford, N.Y.

[22] Filed: May 7, 1974

[21] Appl. No.: 467,671

[52] U.S. Cl. .................................. 204/195 R; 324/29
[51] Int. Cl.[2] ........................................ G01N 27/46
[58] Field of Search ................ 204/1 T, 195 R, 1 N

[56] References Cited
UNITED STATES PATENTS

| | | | |
|---|---|---|---|
| 2,414,411 | 1/1947 | Marks | 204/195 R |
| 3,622,487 | 11/1971 | Chand et al. | 204/195 P |
| 3,719,564 | 3/1973 | Lilly et al. | 204/195 S |
| 3,763,025 | 10/1973 | Chand | 204/1 N |
| 3,776,832 | 12/1973 | Oswin et al. | 204/195 R |
| 3,824,167 | 7/1974 | Oswin et al. | 204/195 R |

*Primary Examiner*—T. Tung
*Attorney, Agent, or Firm*—Larson, Taylor and Hinds

[57] ABSTRACT

The present invention relates to a device and method for the detection and measurement of nitrogen dioxide ($NO_2$) and nitric oxide (NO) in a gaseous medium.

9 Claims, 5 Drawing Figures

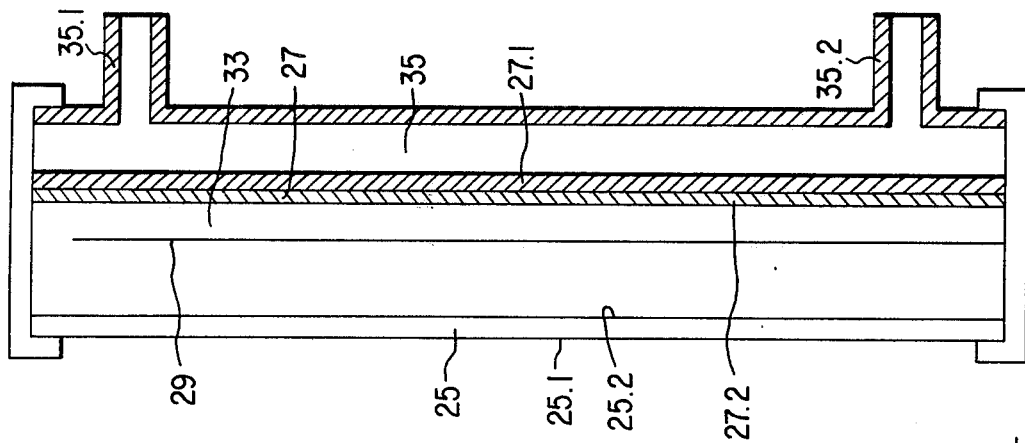
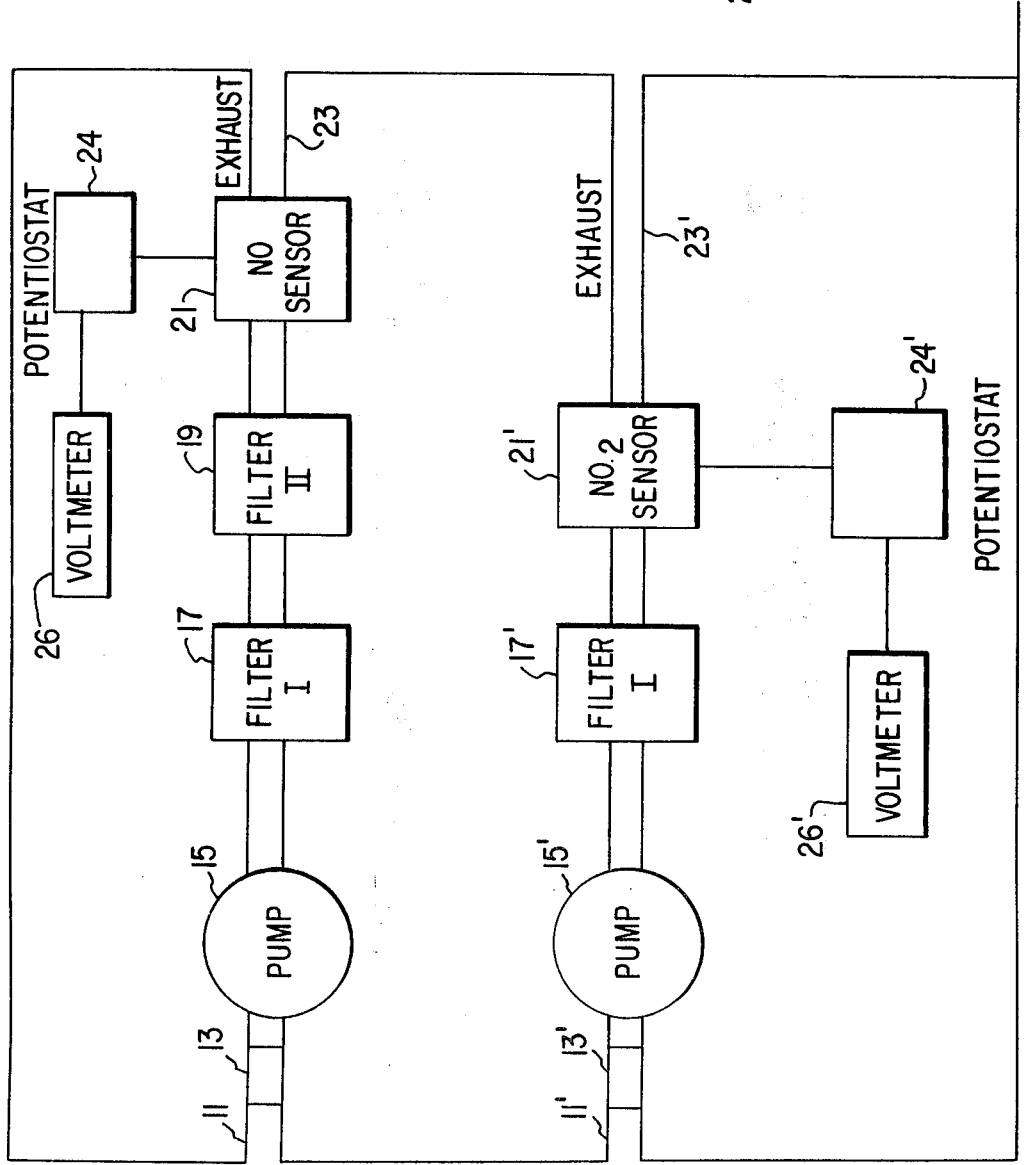

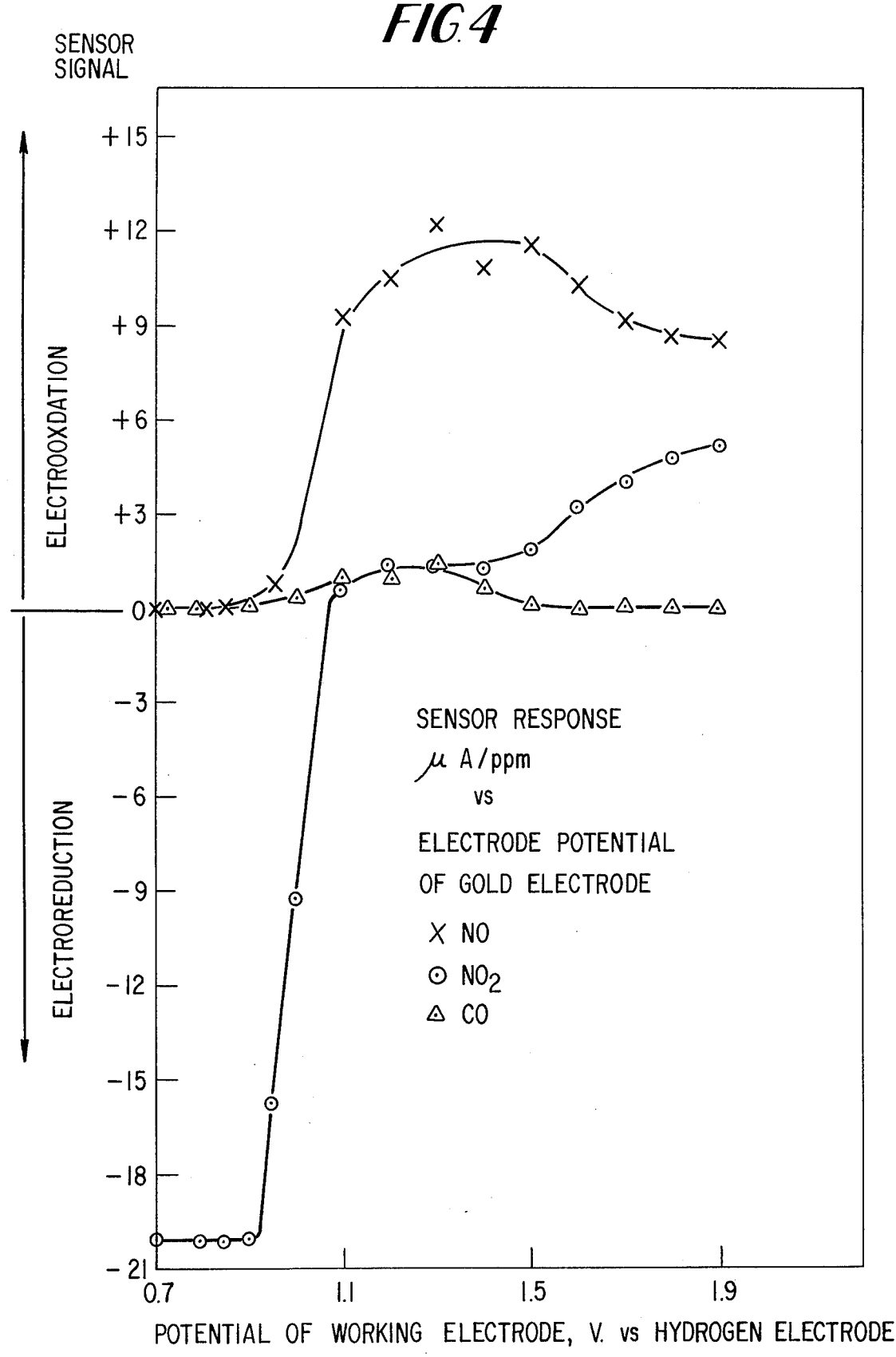

DEVICE FOR THE DETECTION AND MEASUREMENT OF NO AND NO₂ GASES

Discussion of the Prior Art

In recent times, a greater awareness has developed regarding the dangers of air pollution, particularly in urban or industrialized areas. Amongst the principal contributions to air pollution are the products of incomplete combustion such as carbon monoxide, hydrocarbons, carbonaceous particulate matter, etc. Attempts to eliminate these pollutants through more efficient combustion processes has resulted in a frustrating dilemma for the severe oxidation conditions ordinarily employed in more efficient combustion processes increases noxious NO and $NO_2$ gases produced over and above that ordinarily formed as combustion by-products. It is not surprising, therefore, that most major cities yearly average nitrogen dioxide levels are approaching levels known to be harmful to health. As an example of the increasing problem, the ambient air quality standard for nitrogen dioxide has been set at 0.05 ppm for annual average. On high pollution days, however, that concentration of 0.05 ppm is often exceeded by a factor of 4.

In order to meet the needs arising in connection with pollution control of NO and $NO_2$, extensive activity has been directed to the development and production of equipment useful in solving this problem. A problem encountered in the development of such equipment is the difficulties experienced in the detection of low concentrations of NO and $NO_2$ in the presence of high concentrations of CO, a frequently encountered situation. Also, another problem which must be confronted in the search for solutions to this problem is the acknowledged difficulty of measuring NO in the presence of $NO_2$. Although systems may exist which may be considered functionally successful, actual utilization in practical applications has quite often been thwarted due to the cost or complexity of such equipment.

The general criteria applied to measuring and testing equipment such as that of the present invention include requisites for portability, non-prohibitive cost and accuracy in measuring the quantity of the gas detected. In the prior art, it has been found difficult to simultaneously fulfill all of these requirements. Increasing the accuracy of the measuring equipment has inherently involved an increase in either the size or the complexity of such equipment thereby disadvantageously affecting either the cost or portability or both. Quite often, problems related to the simultaneous provision of these features have been decisive in obstructing the practical development and utilization of particular detection apparatus.

OBJECTS AND GENERAL DESCRIPTION OF THE INVENTION

Accordingly, a primary object of the present invention is to provide a compact, inexpensive, and easy-to-operate device for accurately and reproducibly detecting and quantitatively determining the level of NO or $NO_2$ in a specific environment.

Another object of this invention is to provide a compact, inexpensive, and easy-to-operate device for accurately and reproducibly detecting and quantitatively determining the low concentrations of NO and/or $NO_2$ in the presence of high concentrations of CO.

It is another object of this invention to provide a device for accurately measuring low concentrations of NO and $NO_2$ in the presence of each other.

Another object of the this invention is to provide methods for electrochemically detecting low concentrations of NO and/or $NO_2$ in a gaseous medium.

The aforesaid objects of the present invention are obtained by a gas detecting and measuring unit comprising a combination intake means, an electrochemical cell, means for drawing a gas through said intake means and into and through said electrochemical cell at a controlled flow rate, and read-out means for reading the quantity of detected gas. The electrochemical cell comprises a working electrode which may be either an anode or cathode, depending upon whether NO or $NO_2$ is being detected, which working electrode provides a catalytic site for electrochemical reaction with the gas being detected; a counterelectrode, a reference electrode, and an electrolyte in contact with the working electrode, counterelectrode and reference electrode. The working electrode of the cell is maintained by suitable means such as a potentiostat at a fixed potential relative to the potential of the reference electrode, which is substantially free of current flow, to ensure that the current production is a result of the gas being detected and not other gases. The device includes means for exposing the working electrode to the gas to be detected. The fixed potential depends upon whether NO or $NO_2$ is being detected but in either case is selected so that the gas being detected is electrochemically reacted, precluding the possibility that other gases in the sample, such as $O_2$, $H_2O$ vapor, methane, ethane, propane, hydrogen, sulfur oxide, carbon monoxide, etc., will influence the current produced.

When the gas to be detected is NO the working electrode is an anode maintained at a fixed potential relative to the reference electrode of about 0.9 V to 1.9 V, preferably about 1.4 to about 1.7, with respect to a reversible hydrogen electrode in said electrolyte. On the other hand, when the gas to be detected is $NO_2$, the working electrode is a cathode maintained at a fixed potential relative to the reference electrode of about 0.7 V to 1.1 V, preferably about 0.75 to 0.95, with respect to the reversible hydrogen electrode in said electrolyte.

The means for drawing gas through the intake means into the cell with effectively pass a predetermined quantity of gas per unit time to a predetermined working electrode surface area, thus assuring continuous accuracy in the quantitative measurement. Preferably, the quantity of gas fed to the working electrode surface is controlled by a constant flow control means of the conventional type which feeds the gas sample to the electrochemical cell at a constant rate with the balance of the gas sample being vented off. Pumping or suction means are normally employed to draw the gas sample through the intake means, the electrochemical cell, and flow control means in metered amounts. Preferably the working electrode chamber will define a labyrinthine path as is described in the electrochemical cell of U.S. Pat. No. 3,776,832, hereby incorporated by reference, through which the gas sample is passed to the working electrode surface. Other designs can be employed, it only being essential that the geometric working electrode surface area remains constant, or substantially constant, and is fed with a predetermined quantity of gas over a predetermined period of time. In this regard it is to be noted that insofar as the actual gas being detected is concerned, it is immaterial whether the flow rate is high or low.

In a preferred aspect, the device of the invention comprises both a NO and $NO_2$ detecting and measuring unit. In this instance the device comprises in combination, an intake means for the gas medium containing the gas to be detected, a first electrochemical cell for the detection of $NO_2$, a second electrochemical cell for detecting NO, means for drawing the gas medium containing the gas to be detected through the intake means and said first and second electrochemical cells at a controlled rate, read out means for reading the quantity of detected NO and $NO_2$ gas. The first electrochemical cell (NO Sensor) comprises an anode, a cathode, a reference electrode at which substantially no current flows and an aqueous electrolyte in an electrolyte chamber, said electrolyte being in contact with the anode, cathode and reference electrode, means for exposing the anode to NO-containing gaseous medium and means for maintaining the anode at a fixed potential relative to the reference electrode of about 0.9 V to 1.9 V, preferably 1.4 to 1.7, with respect to a reversible hydrogen electrode in the electrolyte.

The second electrochemical cell ($NO_2$ Sensor) likewise comprises an anode, a cathode, a reference electrode at which substantially no current flows, an aqueous electrolyte in a chamber, said electrolyte contacting the three electrodes except that the cathode is the working electrode. Accordingly, means are provided for exposing the cathode to $NO_2$-containing gaseous medium. The $NO_2$ detecting system therefore contains means for maintaining the cathode, rather than the anode at a fixed potential relative to the reference electrode of about 0.7 V to 1.1 V, preferably 0.75 to 0.95, with respect to a reversible hydrogen electrode in the electrolyte.

The anode of the first electrochemical cell is comprised of gold catalyst, capable of catalyzing electrooxidation of NO bonded to a suitable hydrophobic material, such as unsintered polytetrafluoroethylene (PTFE) to provide a lightweight diffusion electrode. The hydrophobic material may take the form of a binder for the gold catalyst, a sheet support therefor or both. For instance, catalytic material may be deposited as a layer directly to the surface of a hydrophobic sheet support or the catalytic material may be admixed with a suitable hydrophobic binder and the admixture applied as a layer to a suitable support as, for instance, a suitable hydrophobic material such as PTFE, carbon or a metal. When an admixture of catalyst and hydrophobic binder is employed it can be supported with any suitable porous support substrate say of plastic, carbon, metal and the like. Suitable hydrophobic binder and/or support substrate materials include hydrophobic fluorocarbons such as polytetrafluoroethylene, polychlorotrifluoroethylene or the like, as well as less hydrophobic materials including polyacrylonitrile, polyvinylchloride polyvinylalcohol, carboxymethyl cellulose, or the like. As will be further apparent to one skilled in the art, when the support substrate, is a hydrophobic material such as PTFE, the hydrophobic material must be oriented in the cell in order that the catalyst is in contact with the gas sample, with the catalytic layer being in contact with the elctrolyte.

The cathode of the second electrochemical cell, that is, the $NO_2$ sensor, is comprised of catalyst capable of catalyzing electroreduction of the $NO_2$ gas being detected, and suitable hydrophobic material such as described above in relationship to the anode of the NO Sensor. Likewise, bonding of the catalytic material to the support may be effected by deposition of the catalytic material onto the hydrophobic support or by application of an admixture of the catalyst and a suitable binder such as described above to a support. The preferred catalytic materials are noble metals and especially preferred is gold.

The specific structure of the counter electrode, that is, the cathode in the NO Sensor and anode in the $NO_2$ sensor, which is employed in the electrochemical cell again is not critical. It is only essential for the NO Sensor that the counter electrode consist of a material at which electrochemical reduction occurs and for the $NO_2$ sensor that it consist essentially of a material at which electrochemical oxidation occurs. The preferred counter electrode for the NO sensor is one which provides a site at which oxygen will be electrochemically reduced as, for example, gold and for the $NO_2$ sensor the preferred counter electrode is one which provides a site at which $H_2O$ is electrochemically oxidized as, for example, gold.

The reference electrode of the electrochemical cell must be capable of maintaining a relatively constant potential in the environment of the electrochemical cell. Preferred reference electrodes are Au-catalyzed air electrodes. The third or reference electrode can be positioned between the anode and cathode, or it can be positioned behind either the anode or cathode or on the same plane or substrate as the cathode or anode. Preferably, however, in order to obtain greater compactness of the cell and due to optimum ion-transfer characteristics, and the like, the cathode and the third or reference electrode will be part of a common substrate. It is only necessary that the anode, cathode, and third electrode be electrically insulated from each other. Thus, a polymer substrate such as polytetrafluoroethylene can have two separate and distinct portions coated with a catalytic material such as platinum black, or an admixture of platinum black and PTFE particles. The entire substrate will, therefore, function as both the cathode and reference electrode. As will be more fully apparent hereinafter, various designs or lay-outs can be used.

Reference electrode, as the term is used herein, defines an electrode at which no, or substantially no, current flows. Accordingly, the reference electrode and working electrode must be connected through electronic circuitry, or the like, to preclude or minimize current flow between the reference electrode and working electrode, so as to define and maintain a known reference potential. Although it is virtually impossible to completely eliminate current flow, the reference potential cannot show extensive drift, i.e., more than about ± 25 mV; or rapid drift, i.e., more than ±5 mV, over a period of ten seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated.

When the gaseous medium contains both NO and $NO_2$, as for instance air, and the gas desired to be detected is NO, a filter or scrubber means should be employed between the sample intake and the electrochemical cell (NO Sensor) to remove $NO_2$. $NO_2$ tends to electrooxidize and give a signal at 1.6 V, which is the optimum potential at which the anode is fixed for the detection of NO. Illustrative of suitable filters or scrubbers are absorbents such as activated carbon, alumina, Mallcosorb and the like.

Advantageously, similar other scrubbers or filters are provided between the sample intake and both electrochemical cells for the removal of other interfering gases such as $H_2S$ that may be present in the gaseous medium and which give signals at the fixed potentials. $H_2S$ gives approximately the same signal as NO at 1.6 V and as $NO_2$ at 0.85 V and should be removed from gas samples containing same before measurement. Suitable $H_2S$ filters include, for instance, lead acetate and mercuric chloride filters. In addition, carbon, alumina and Mallcosorb are recognized $H_2S$ filters but since they also absorb $NO_2$, they cannot be used when it is desired to measure $NO_2$.

As will be fully apparent to one skilled in the art one of the essential features of the invention is the selection of the proper working electrode and maintaining the working electrode at the defined fixed potentials relative to the hydrogen electrode as a zero base with reference to the third or reference electrode as hereinbefore defined. The potential of the NO cell is maintained in the range of about 0.9 V to 1.7 V versus the reversible hydrogen electrode with the optimum potential being about 1.6 V. This potential was found to give a maximum signal for NO and a minimum signal for water, $NO_2$ and CO oxidation and oxygen reduction. The potential of the $NO_2$ cell, on the other hand, is maintained in the range of 0.7 V to 1.1 V versus the reversible hydrogen electrode with the optimum being 0.85 V. This potential was found to give a maximum signal for $NO_2$ and minimum signal for NO, CO and water oxidation and oxygen reduction. Also, due to the choice of the electrode potentials, it was found the following gases give negligible signals at the optimum potentials of either the NO or $NO_2$ cell. CO, $CH_4$, $C_3H_8$, $C_2H_4$, $SO_2$ and $H_2$.

The working electrode should have a fixed geometric surface area available to the gaseous reactant which is fed at a controlled flow. This is preferably accomplished by using a labyrinthine path or by utilizing a fan for flowing the reactant gas to the electrode surface.

The housing of the electrochemical cells can be made of any suitable material which does not form soluble oxidizable products, preferably plastics such as the olefinic polymers. The housing is to be designed to permit the working electrode to have an area exposed to ambient air. The electrolyte which can be either an aqueous acid or aqueous alkaline solution can be freeflowing or trapped in a suitable matrix. In the event a matrix is employed, the matrix material must be sufficiently hydrophilic to permit continuous wetting of the anode and cathode surfaces as well as the surface of the third or reference electrode. Materials such as asbestos, Kraft paper, polyvinylalcohol, polyvinylchloride which has been treated to render it hydrophilic, or the like, can be selected.

In addition to the electrochemical cell, it is necessary that the detecting device include sample intake means and means to control the flow of the gas sample through the cell. The control of the flow rate of the sample can be accomplished in various ways. Thus, the gas sample is received through the intake means of the detecting device and pulled into the electrochemical cell, preferably by means of a suitable pump. The flow rate can be controlled in various ways including a restricted intake orifice positioned between the pump means and the intake means. The flow meter and pump can be of various commercial design and form no part of the present invention. The only criterion is that the pump means have sufficient capacity to pull the gas sample through the electrochemical cell and flow meter. The flow meter must have precision sufficient to measure the volumn being carried through the electrochemical cell with reasonable accuracy.

BRIEF DESCRIPTION OF THE DRAWINGS

The detecting device of the present invention will be more readily apparent from the accompanying drawing wherein like numerals are employed to designate like parts.

In the drawing:

FIG. 1 is a diagrammatic view in block form of a preferred device suitable for use in the detection and measuring of both NO and $NO_2$ in the atmosphere, FIG. 2 is a cross-sectional view of an electrochemical cell useful in the detector unit;

FIG. 4 is a graph described above showing the significance of the fixed potential of the invention;

DETAILED DESCRIPTION OF PREFERRED EMBODIMENT

Figure 3:
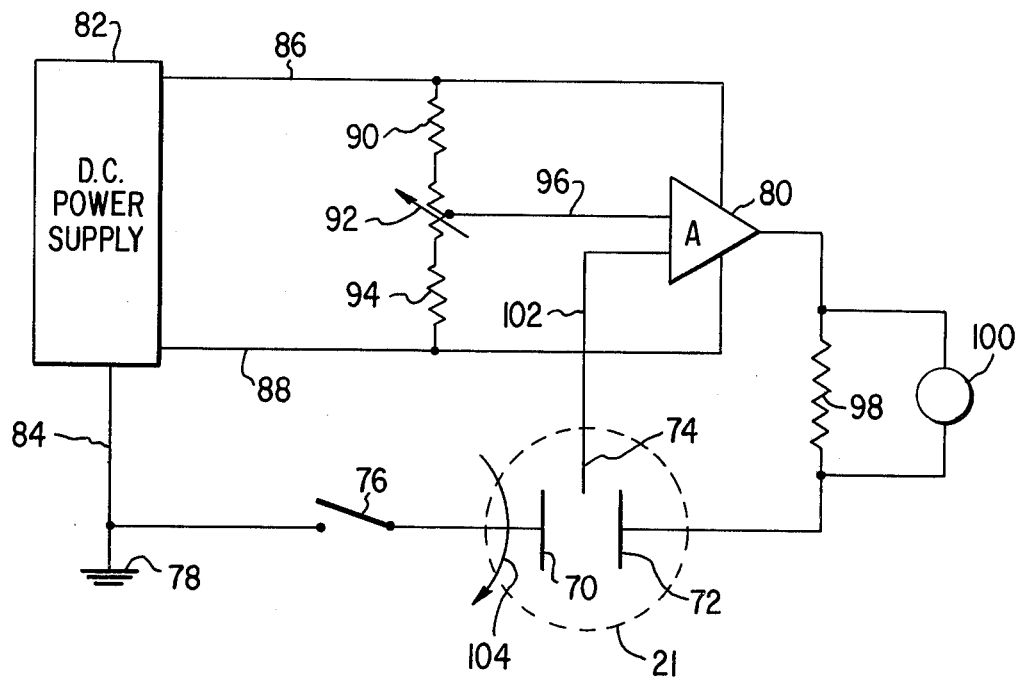
FIG. 3 is a schematic diagram of a potentiostat circuit for controlling operation of the cell and particularly as applied in maintaining a fixed potential between the working electrode and a reference electrode.
Figure 5:
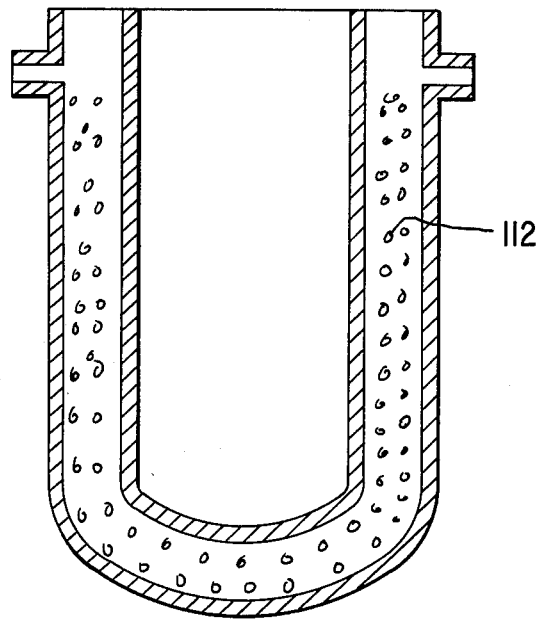
FIG. 5 is a filter unit for incorporation in the device of FIG. 2.

More specifically, referring to FIG. 1, the detecting device 1 is positioned within a housing 10. The device includes a first sample intake means 11 in direct communication with a flow meter 13 which in turn is in communication with a pump 15. The pump 15 communicates with a Filter I designated 17 containing, for instance, mercuric chloride for the absorption of $H_2S$. Filter I is in direct communication with Filter II, designated 19, containing, for instance, activated alumina, for the absorption of $NO_2$ and Filter II in turn is in direct communication with NO sensor 21. Gas flowing through the NO sensor 21 exits device 1 via exhaust 23. The NO sensor is provided with a potentiostat 25 for maintenance of the fixed relative potential between the anode and the reference electrode of NO sensor 21 and a voltmeter 26. The potentiostat is hooked up to an electronic circuit described below which includes an amplifier and voltmeter.

The device 1 also contains a separate system for the detection and measurement of $NO_2$ which includes a second sample intake 11' communicating directly with a flow control meter 13' which in turn communicates with a pump 15'. The pump 15' is connected to a Filter 17' which like Filter I contains an absorbent for $H_2S$. Filter 17' is in direct communication with $NO_2$ sensor 21' and gas flowing through this sensor exits via exhaust 23'. It similarly has a potentiostat 24' and a voltmeter 26'.

Both electrochemical cells 21 and 21', as seen most clearly from FIG. 2, will include a counter electrode 25, a working electrode 27, and a third or reference electrode 29, all positioned within a housing 31. In the embodiment of FIG. 2, the counter electrode, working electrode, and third electrode are in contact with a freeflowing electrolyte 33. Adjacent anode 27 is reactant chamber 35 having reactant gas inlet 35.1 which is in direct communication with intake 11 and outlet 35.2. In the embodiment shown, counter electrode 25 is in direct communication with atmospheric air. Both the working electrode and counter electrode are lightweight electrodes comprising a hydrophobic plastic substrate 27.1 and 25.1 in direct contact with reactant chamber 35 in the case of the working electrode, and with the ambient environment in the case of the counter electrode, and catalytic layers 27.2 which comprise a mixture of gold powder and polytetrafluoroethylene particles and 25.2 which comprise a mixture of platinum and polytetrafluoroethylene particles. The catalyst layers are in contact with the electrolyte of the cell. The gold is present in a loading of preferably 5–50, more preferably 5–30 mg/cm$^2$. The ratio of gold to PTFE is preferably 10 to 3 on a weight basis. Reference electrode 29 is a porous, platinum catalyzed PTFE diffusion electrode which is approximately 7 mils thick. For the NO sensor a fixed potential of 1.6 volts with respect to a reversible hydrogen electrode in the same electrolyte is maintained on the working electrode by means of the reference electrode through the potentiostat 25. The working electrode, counter electrode and reference electrode of the cell are connected through the electrical circuit, shown in FIG. 3. In the case of the NO sensor the cell is connected to the circuitry so that the polarity of the working electrode (anode) to the counter electrode (cathode) is positive. With the $NO_2$ sensor the connection is reversed so that the polarity of the working electrode (cathode) to the counter electrode (anode) is negative.

The circuitry whereby the maintenance of a fixed relative potential between the working electrode and reference electrode is shown in FIG. 3. FIG. 3 depicts a potentiostat circuit which is generally arranged in accordance with conventional principles within the knowledge of these skilled in the art and which enables the maintenance of the fixed relative potential between the working electrode and the reference electrode without development of current flow therebetween. The circuit also operates to enable appropriate current flow in the external circuit between the working electrode and the counter electrode when the gas to be detected is reacted within the electrochemical cell.

In FIG. 3, the anode detecting electrochemical cell 21 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92, and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 74 is connected to the operational amplifier 80 through a lead 102 and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anodereference electrode fixed relative potential is developed as a result of reaction at the anode 70 of the impurity to be detected, i.e. oxidation of NO contained therein the gas sample flowing across the face of the anode 70 as indicated by the arrow 104. The output current of the operational amplifier 80 will pass through the resistor 98 and will be a result of and related to the level of oxidation of NO occurring at the anode 70. Therefore, the reading taken at the voltmeter 100 will be representative of the oxidation reaction occurring at the anode 70 and the quality of material oxidized. The voltmeter 100 may be readily calibrated in the known manner to provide determination of the quantity of NO occurring in the air sample taken, and if the conditions in the anode chamber are in accordance with the teachings previously set forth, appropriate readings may be generated pursuant to the principle of operation provided.

The $NO_2$ detecting electrochemical cell is similarly constructed and functions in the same manner except as aforementioned the circuitry is connected so that the polarity of the working electrode to the counterelectrode is negative. The working electrode then becomes the cathode and the counterelectrode becomes the anode.

The significance of the fixed potential which is maintained between the working electrode and the reference electrode is better described by reference to the chart of FIG. 4 wherein the signal due to NO, $NO_2$ and CO is shown as a function of the potential. The graph shows that at 0.85 V the signals (the current) due to NO and CO are negligible while the signal due to $NO_2$ is large. Also, the graph shows that at 1.6 V essentially the signal due to CO is negligible, the signal due to $NO_2$ is small and the signal due to NO is relatively large.

In operation, therefore, assuming the desirability of measuring the concentration of NO and $NO_2$ in the atmosphere, the atmospheric air containing the noxious impurities is introduced at a metered rate into the respective sensors NO and $NO_2$. The sample entering the NO has passed through filters 17 and 19 for removal of $H_2S$ and $NO_2$ whereas the atmospheric air sample passing into $NO_2$ sensor 21' has had removed from it $H_2S$ by means of filter 17'. In the NO sensor the air sample passes over the anode therein setting off electrooxidation of the NO impurity contained therein. This electrochemical reaction produced a current in the external circuit of the cell thereby enabling detection and measurement of the impurity concentration as by use of a voltmeter. In the $NO_2$ detection system, the air sample passes over the cathode thereby effecting an electroreduction of the $NO_2$ impurity contained therein. The electroreduction reaction also produces a current which is similarly measured to enable determination of the connection of $NO_2$ in the air.

Although FIG. 1 has been represented as containing two entirely separate systems for the detection of NO and $NO_2$ respectively, it should be understood that the invention is not limited thereto but contemplates numerous modifications which would be obvious to those of ordinary skill in the art. For instance, should it not be essential to obtain simultaneous measurements of NO and $NO_2$ impurities in a gaseous medium the device may contain a single intake, pump, filters and exhaust with the connecting means appropriately modified with valves or other directing means as will be apparent to those skilled in the art. Two other possible arrangements for simultaneous measurements comprises a single intake and pump utilizing a split stream of gas or a single intake and pump with the gas going sequentially through the $NO_2$ cell and then the NO cell.

It is claimed:

1. An $NO_2$ detecting and measuring unit comprising in combination an intake means, an electrochemical cell, means for drawing an $NO_2$ containing gas through said intake means and into said electrochemical cell at a controlled flow rate, read out means for reading the quantity of $NO_2$ gas described, said electrochemical cell comprising an anode, a cathode, a reference electrode at which substantially no current flows and an aqueous electrolyte in contact with said anode, cathode and reference electrode, means for exposing said cathode to said $NO_2$ containing gas, means for maintaining said cathode at a fixed potential relative to the reference electrode of about 0.7 V to 1.1 V with respect to a reversible hydrogen potential in said electrolyte, electrical circuitry connected so that the polarity of the cathode to the anode is negative, the cathode of said electrochemical cell comprising a catalyst capable of catalyzing the electroreduction of $NO_2$ at said fixed potential bonded to a hydrophobic material to provide a diffusion electrode.

2. The device of claim 1 wherein the catalyst comprises gold.

3. The device of claim 1 wherein the hydrophobic material is a hydrophobic fluorocarbon.

4. The device of claim 3 wherein the hydrophobic fluorocarbon is polytetrafluoroethylene.

5. The device of claim 1 provided with means between the intake and said electrochemical cell for the removal of $H_2S$ gas.

6. An NO and $NO_2$ detecting and measuring unit comprising in combination a first intake means, a first electrochemical cell, means for drawing an NO containing gas through said intake means and into said electrochemical cell at a controlled flow rate, read out means for reading the quantity of NO gas detected, the first electrochemical cell comprising an anode, a cathode, a reference electrode at which substantially no current flows and an aqueous electrolyte in contact with said anode, cathode and reference electrode, means between said intake means and said first electrochemical cell for removing $NO_2$, means for exposing said anode to said NO-containing gas, means for maintaining said anode at a fixed potential relative to the reference electrode of about 0.9 V to about 1.9 V with respect to a reversible hydrogen electrode in said electrolyte of said first electrochemical cell, the anode of said first electrochemical cell comprising a catalyst capable of catalyzing electrooxidation of NO at said first potential bonded to a hydrophobic material to provide a diffusion electrode, a second intake means, a second electrochemical cell, a second means for drawing an $NO_2$-containing gas through said second intake means in said second electrochemical cell at a controlled flow rate, a second read out means for reading the quantity of detected $NO_2$ gas, said second electrochemical cell comprising a second anode, a second cathode, a second reference electrode at which no current flows and an aqueous electrolyte in contact with said second anode, second cathode and second reference electrode, means for exposing said second cathode to the $NO_2$-containing gas, means for maintaining said second cathode at a fixed potential relative to the second reference electrode of about 0.7 V to 1.1 V with respect to a reversible hydrogen electrode in said electrolyte of said second electrochemical cell, electrical circuitry connected so that the polarity of the second cathode to the second anode is negative, the cathode of said second electrochemical cell comprising catalyst capable of catalyzing the electroreduction of $NO_2$ at said fixed potential bonded to a hydrophobic material to provide a diffusion electrode.

7. The device of claim 6 wherein the hydrophobic material of the anode in the first electrochemical cell and the hydrophobic material of the cathode of said second electrochemical cell is a hydrophobic fluorocarbon.

8. The device of claim 7 wherein the hydrophobic fluorocarbon is polytetrafluoroethylene.

9. The device of claim 7 wherein the catalyst of said anode of said first cell is gold and the catalyst of said cathode of said second cell is gold.

* * * * *